US00PP24563P3

(12) United States Plant Patent
Egger

(10) Patent No.: US PP24,563 P3
(45) Date of Patent: Jun. 17, 2014

(54) ***HEUCHERA* PLANT NAMED 'PEPPERMINT'**

(50) Latin Name: ***Heuchera* hybrid**
Varietal Denomination: Peppermint

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 141 days.

(21) Appl. No.: 13/507,993

(22) Filed: Aug. 10, 2012

(65) Prior Publication Data

US 2014/0047609 P1 Feb. 13, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by small, lightly veiled, deep green leaves, very short flowering stems of pink flowers, reblooming all spring, summer, and fall, small, multi-crowned, low mounding habit, and good vigor.

1 Drawing Sheet

Botanical denomination: *Heuchera* hybrid.
Variety designation: 'Peppermint'.

BACKGROUND OF THE INVENTION

The present invention relates to a new and distinct cultivar of *Heuchera* and given the cultivar name of 'Peppermint'. *Heuchera* is in the family Saxifragaceae. *Heuchera* 'Peppermint' is the end product of a planned breeding program to create miniature *Heuchera* for small pots. This new cultivar originated from a cross between *Heuchera* K413-1, a proprietary non-commercial hybrid, as the seed parent, and *Heuchera* K388-4, a proprietary non-commercial hybrid, as, as the pollen parent.

Compared to the seed parent, *Heuchera* K413-1, the new cultivar has leaves that are green rather than amber and pink rather than white.

Compared to the pollen parent, *Heuchera* K388-4, the new cultivar has green leaves rather than red purple leaves.

Compared to *Heuchera* 'Paris', U.S. Plant Pat. No. 18,881, the new cultivar has a much smaller habit, smaller flowers, and smaller darker green leaves.

This new *Heuchera* is uniquely distinguished by:

1. small, lightly veiled, deep green leaves,
2. very short flowering stems of pink flowers,
3. reblooming all spring, summer, and fall,
4. small, multi-crowned, low mounding habit, and
5. good vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a nine-month-old plant of the new cultivar growing in a half gallon container in a cool greenhouse in July in Canby, Oreg.

DETAILED PLANT DESCRIPTION

The following is a detailed description of the new *Heuchera* cultivar based on observations of two-year-old specimens growing in half gallon containers in a cool greenhouse in April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—10 cm tall from top of the foliage to the ground and 22 cm wide.
*Habit.*—Mounding.
*Vigor.*—Good.

Leaf:

*Type.*—Simple.
*Arrangement.*—Rosette.
*Shape.*—Broadly ovate to orbicular.
*Number.*—About 60.
*Lobing/division.*—5 to 7 lobes.
*Venation.*—Palmate.
*Margins.*—Crenate.
*Apex.*—Mucronulate.
*Base.*—Cordate and overlapping.
*Blade size.*—Grows to 5 cm long and 4.5 cm wide.
*Surface texture.*—Glandular on top and bottom.

*Petiole description.*—Grows to 8 cm long and 1.5 mm wide, glandular hairs, Yellow Green 146A.

*Leaf color.*—Topside, spring leaves Green 137A darkening to Green 139A some with a veil depending on environmental conditions, White NN155C; winter leaves Green 139A with veil White NN155C and dark veins; bottom side Yellow Green 147B.

Inflorescence:

*Size.*—Grows to 3 cm wide and 5.5 cm long.

*Type.*—Thyrse.

*Number of flowers per thyrse.*—About 60.

*Number of thyrse.*—About 30 in the first spring flush, reblooming all summer.

*Peduncle.*—Grows to 17 cm long, 2 mm wide at base, glandular hairs, Yellow Green 147A.

*Pedicel.*—Variable in size, with glandular hairs, Greyed Red 178A.

*Bloom period.*—April through October in Canby, Oreg.

Flower bud:

*Size.*—2 mm wide and 4 mm long.

*Description.*—Glandular puberulent, ovoid, down facing.

*Color.*—Red Purple 58D.

Flower:

*Type.*—Perfect.

*Shape.*—Campanulate.

*Size.*—5 mm long and 2.3 mm wide.

*Corolla description.*—5 petals, 2 mm long and 0.5 mm wide, reflexed, narrowly spatulate, margins entire, tip acute, glabrous top and glandular on bottom, Red Purple 58D.

*Calyx description.*—Campanulate, 5 mm long and 2.3 mm wide, with 5 lobes divided ½ way to the base, each 1 mm wide and 2 mm long, glandular hairs outside and glabrous inside, tips obtuse, margin entire; color both sides Red Purple 62B.

*Stamen description.*—5 in number, filaments 1.5 mm long, White NN155C, anthers 0.2 mm, Orange 29B, no pollen, male sterile.

*Pistil description.*—1, 2-beaked, 5 mm long and 1.5 mm wide; ovary 1.5 mm long and 1.5 mm wide, Yellow White 158D, style 2.5 mm long, White NN155C.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

*Size.*—4 mm long and 3 mm wide.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

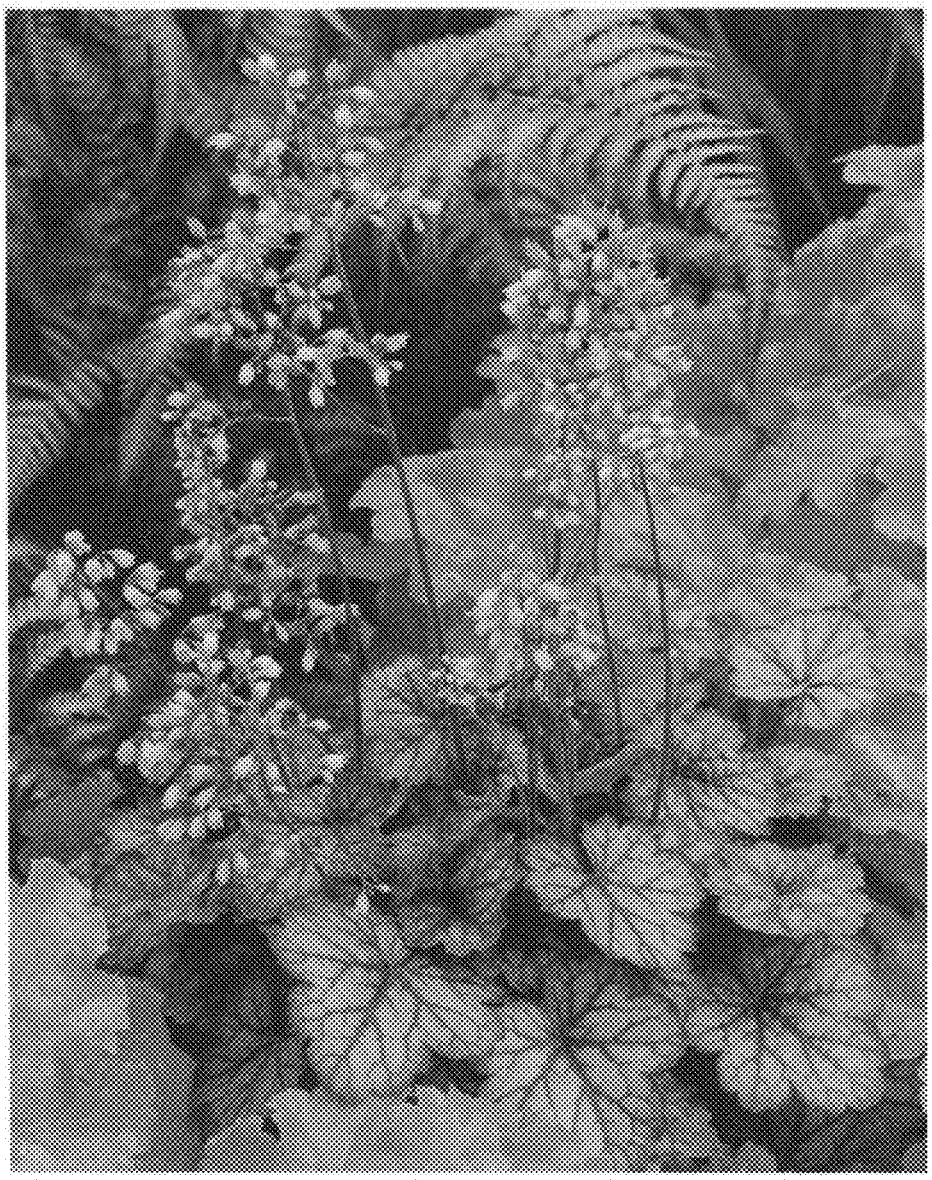

* * * * *